United States Patent
Lewandowski et al.

(10) Patent No.: US 6,762,257 B1
(45) Date of Patent: Jul. 13, 2004

(54) AZLACTONE CHAIN TRANSFER AGENTS FOR RADICAL POLYMERIZATION

(75) Inventors: Kevin M. Lewandowski, Inver Grove Heights, MN (US); Duane D. Fansler, Dresser, WI (US); Michael S. Wendland, North Saint Paul, MN (US); Steven M. Heilmann, Afton, MN (US); Babu N. Gaddam, Woodbury, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 10/429,487

(22) Filed: May 5, 2003

(51) Int. Cl.[7] .................................................. C08F 4/06
(52) U.S. Cl. ........................ 526/146; 526/135; 526/147; 526/204; 526/220; 525/308; 525/314
(58) Field of Search ................................ 526/135, 146, 526/204, 220, 147; 525/308, 314

(56) References Cited

U.S. PATENT DOCUMENTS

| | | |
|---|---|---|
| 5,763,548 A | 6/1998 | Matyjaszewski et al. |
| 6,143,848 A | 11/2000 | Lee et al. |
| 6,153,705 A | 11/2000 | Corpart et al. |

FOREIGN PATENT DOCUMENTS

| | | |
|---|---|---|
| WO | WO 97/18247 | 5/1997 |
| WO | WO 99/31144 | 6/1999 |
| WO | WO 02/26836 A3 | 4/2002 |
| WO | WO 02/26836 A2 | 4/2002 |

OTHER PUBLICATIONS

A. Šebenik, "Living Free–Radical Block Copolymerization Using Thio–Iniferters", Prog. Polym. Sci., (1998), pp. 875–917, vol. 23.

"Polyazlactones", Encyclopedia of Polymer Science and Engineering, (1988), pp. 558–571, vol. 11, $2^{nd}$ Edition, John Wiley and Sons.

S. M. Heilmann, "Chemistry and Technology of 2–Alkenyl Azlactones", Journal of Polymer Science: Part A: Polymer Chemistry, (2001), pp. 3655–3677, vol. 39, John Wiley and Sons, Inc.

Y. K. (Bill) Chong, "A More Versatile Route to Block copolymers and Other Polymers of Complex Architecture by Living Radical Polymerization: The RAFT Process", Macromolecules, (1999), pp. 2071–2074, vol. 32, American Chemical Society.

M. Freemantle, "In Control of a Living Process", Chemical and Engineering News, (Sep. 9, 2002) pp. 36–40.

G. B. Fields et al., "Solid Phase Peptide Synthesis Utilizing 9–fluorenylmethoxycarbonyl Amino Acids", International Journal of Peptide & Protein Research, (1990), pp. 161–214, vol. 35.

G. B. Fields et al., Chapter 3, "Principles and Practice of Solid–Phase peptide Synthesis", Synthetic Peptides: A User's Guide, G. A. Grant Edition, (1992), pp. 77–183, W. H. Freeman and Co., New York, NY.

*Primary Examiner*—Tatyana Zalukaeva
(74) *Attorney, Agent, or Firm*—Kent S. Kokko

(57) ABSTRACT

Chain transfer agents for controlled radical polymerizations (RAFT) are described. The chain transfer agents have an azlactone or ring-opened azlactone moiety to provide telechelic (co)polymers.

16 Claims, No Drawings

AZLACTONE CHAIN TRANSFER AGENTS FOR RADICAL POLYMERIZATION

FIELD OF THE INVENTION

The present invention provides initiators for reversible addition-fragmentation chain transfer (RAFT) polymerization processes and telechelic polymers made thereby.

BACKGROUND

In conventional radical polymerization processes, the polymerization terminates when reactive intermediates are destroyed or rendered inactive; radical generation is essentially irreversible. It is difficult to control the molecular weight and the polydispersity (molecular weight distribution) of polymers produced by conventional radical polymerization, and difficult to achieve a highly uniform and well-defined product. It is also often difficult to control radical polymerization processes with the degree of certainty necessary in specialized applications, such as in the preparation of end functional polymers, block copolymers, star (co)polymers, and other novel topologies.

In a controlled radical polymerization process radicals are generated reversibly, and irreversible chain transfer and chain termination are absent. There are four major controlled radical polymerization methodologies: atom transfer radical polymerization (ATRP), reversible addition-fragmentation chain transfer (RAFT), nitroxide-mediated polymerization (NMP) and iniferters, each method having advantages and disadvantages.

RAFT processes are among the most versatile controlled radical polymerization techniques, as reported by M. Freemantle, Chemical and Engineering News, Sep. 9, 2002, pp. 36–40. In a RAF process a propagating polymer radical ($P_m$•) adds to a chain transfer agent ($P_n$-X) to generate a new radical intermediate ($P_m$-X•-$P_n$). This intermediate radical fragments either to a new propagating radical ($P_n$•) and a new dormant species ($P_m$-X), or back to ($P_m$•) and ($P_n$-X). The RAFT chain transfer agent establishes a dynamic addition-fragmentation equilibrium by transferring activity between the propagating radicals and the dormant species. The polymerization may be reactivated by addition of more thermal- or photoinitiator and monomer.

There is a need for a radical polymerization process which provides (co)polymers having a predictable molecular weight and a narrow molecular weight distribution (low "polydispersity"). A further need is strongly felt for a radical polymerization process which is sufficiently flexible to provide a wide variety of products, but which can be controlled to the degree necessary to provide highly uniform products with a controlled structure (i.e., controllable topology, composition, etc.). There is further need for a controlled radical polymerization process which provides telechelic (co)polymers capable of entering into further polymerization or functionalization through reactive end-groups, particularly electrophilic end groups.

SUMMARY OF THE INVENTION

The present invention provides chain transfer agents (RAFT agents) for controlled radical polymerization processes that comprise compounds of the formula:

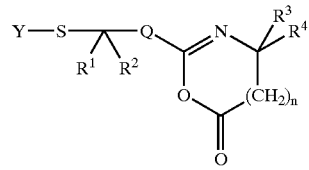

wherein $R^1$ and $R^2$ are each independently selected from H, an alkyl group, a nitrile group, a cycloalkyl group, a hetcrocyclic group, an arenyl group and an aryl group, or $R^1$ and $R^2$ taken together with the carbon to which they are attached form a carbocyclic ring;

$R^3$ and $R^4$ are each independently selected from an alkyl group, a cycloalkyl group, an aryl group, an arenyl group, or $R^3$ and $R^4$ taken together with the carbon to which they are attached form a carbocyclic ring;

Y—S is a xanthate group of the formula $R^5$—O—C(S)—S—, a thioxanthate group (trithiocarbonate) of the formula $R^5$—S—C(S)S—, or a dithioester group of the formula $R^5$—C(S)S—, wherein $R^5$ is selected from an alkyl group, a cycloalkyl group, an aryl group, an arenyl group or a heterocyclic group, $R^5$ is optionally substituted with phosphate, phosphonate, sulfonate, ester, halogen, nitrile, amide, and hydroxy groups; and $R^5$ may optionally be substituted with one or more caternary heteroatoms, such as oxygen, nitrogen or sulfur; Q is a linking group selected from a covalent bond, an arenyl group, an aryl group, (—$CH_2$—)$_o$, —CO—O—($CH_2$)$_o$—, —CO—O—($CH_2CH_2O$)$_o$—, —CO—$NR^8$—($CH_2$)$_o$—, —CO—S—($CH_2$)$_o$—, where o is 1 to 12, and $R^8$ is H, an alkyl group, a cycloalkyl group, an arenyl group, a heterocyclic group, or an aryl group; and n is 0 or 1.

The present invention also provides chain transfer agents that comprise the ring-opened reaction product of the chain transfer agents of Formula I and a reactive compound, such as an aliphatic compound, having one or more nucleophilic groups. Such chain transfer agents have the general formula:

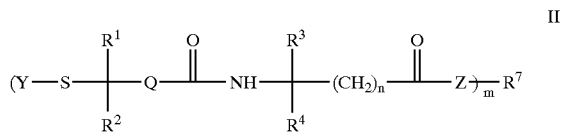

wherein $R^1$ and $R^2$ are each independently selected from H, a nitrile group, an alkyl group, a cycloalkyl group, an arenyl group, a heterocyclic group and an aryl group or $R^1$ and $R^2$ taken together with the carbon to which they are attached form a carbocyclic ring; $R^3$ and $R^4$ are each independently selected from an alkyl group, a cycloalkyl group, an aryl, an arenyl group, or $R^3$ and $R^4$ taken together with the carbon to which they are attached form a carbocyclic ring;

Y—S is a xanthate group of the formula $R^5$—O—C(S)—S—, a thioxanthate group of the formula $R^5$—S—C(S)S—, or a dithioester group of the formula $R^5$—C(S)S—, wherein $R^5$ is selected from an alkyl group, a cycloalkyl group, an aryl group, an arenyl group or a heterocyclic group, $R^5$ is optionally substituted with phosphate, phosphonate, sulfonate, ester, halogen, nitrile, amide, and hydroxy groups; and $R^5$ may optionally be substituted with one or more caternary heteroatoms, such as oxygen, nitrogen or sulfur;

n is 0 or 1;

Z is O, S or $NR^8$, wherein $R^8$ is H, an alkyl group, a cycloalkyl group, an arenyl group, a heterocyclic group, or an aryl group;

$R^7$ is an organic or inorganic moiety and has a valency of m, $R^7$ is the residue of a mono- or polyfunctional compound of the formula $R^7(ZH)_m$;

Q is a linking group selected from a covalent bond, an aryl group, an arenyl group, $(-CH_2-)_o$, $-CO-O-(CH_2)_o-$, $-CO-O-(CH_2CH_2)_o-$, $-CO-NR^8-(CH_2)_o-$, $-CO-S-(CH_2)_o-$, where o is 1 to 12, and $R^8$ is H, an alkyl group, a cycloalkyl group, an aryl group, an arenyl group, a heterocyclic group or an aryl group;

m is an integer of at least 1, preferably at least 2.

The present invention also provides initiator compositions for controlled radical polymerization comprising the chain transfer agents of Formulas I or II, and a thermal or photoinitiator.

The chain transfer agents of the present invention provide (co)polymers having a predictable molecular weight and a narrow molecular weight distribution. Advantageously, the chain transfer agents provide novel multireactive addition polymers having first and second terminal reactive groups that may be used for further functionalization. The present invention further provides a controlled radical polymerization process useful in the preparation of terminal-functionalized (telechelic) (co)polymers, block copolymers, star (co)polymers, graft copolymers, and comb copolymers. The process provides these (co)polymers with controlled topologies and compositions.

The control over molecular weight and functionality obtained in this invention allows one to synthesize numerous materials with many novel topologies for applications in coatings, surface modifications, elastomers, sealants, lubricants, pigments, personal care compositions, composites, inks, adhesives, dental resins, water treatment materials, hydrogels, imaging materials, telechelic materials and the like.

In another aspect, the invention provides a method for polymerization of one or more olefinically unsaturated monomers comprising addition polymerizing one or more olefinically unsaturated monomers using the initiator composition comprising the azlactone chain transfer agents, or the ring-opened azlactone chain transfer agent and a thermal or photoinitiator.

It is to be understood that the recitation of numerical ranges by endpoints includes all numbers and fractions subsumed within that range (e.g. 1 to 5 includes 1, 1.5, 2, 2.75, 3, 3.80, 4, and 5).

It is to be understood that all numbers and fractions thereof are presumed to be modified by the term "about."

It is to be understood that "a" as used herein includes both the singular and plural.

The general definitions used herein have the following meanings within the scope of the present invention.

The term "alkyl" refers to straight or branched, cyclic or acyclic hydrocarbon radicals, such as methyl, ethyl, propyl, butyl, octyl, isopropyl, tert-butyl, sec-pentyl, cyclohexyl, and the like. Alkyl groups include, for example, 1 to 18 carbon atoms, preferably 1 to 12 carbon atoms, or most preferably 1 to 6 carbon atoms.

The term "aryl" means the monovalent residue remaining after removal of one hydrogen atom from an aromatic compound that can consist of one two or three fused rings having 6 to 14 carbon atoms.

The term "arenyl" means the monovalent residue remaining after removal of a hydrogen atom from the alkyl portion of a hydrocarbon containing both alkyl and aryl groups having 6 to 26 atoms.

The term "azlactone" means 2-oxazolin-5-one groups and 2-oxazolin-6-one groups of Formula I, where n is 0 and 1, respectively.

The term "heterocyclic group" or "heterocycle" means the monovalent residue remaining after removal of one hydrogen atom from an cycloaliphatic or aromatic compound having one, two or three fused rings having 5 to 12 ring atoms and 1 to 3 heteroatoms selected from S, N, and nonperoxidic O. Useful heterocycles include azlactone, pyrrole, furan, thiophene, imidazole, pyrazole, thiazole, oxazole, pyridine, piperazine, piperidine, and hydrogenated and partially hydrogenated derivatives thereof The term "multifunctional" means the presence of more than one of the same functional reactive group;

The term "multireactive" means the presence of two or more different functional reactive groups;

The term "polyfunctional" is inclusive of multireactive and multifunctional.

The term "acid catalyst" or "acid catalyzed" means catalysis by a Brønsted- or Lewis-acid species;

The term "molecular weight" means number average molecular weight ($M_n$), unless otherwise specified.

The term (co)polymer refers to homo- and copolymers.

The term (meth)acrylate refers to both methacrylate and acrylate.

The term "telechelic" refers to (co)polymers having a functional group on each terminus.

DETAILED DESCRIPTION

The present invention provides novel chain transfer agents of Formula I and the corresponding ring-opened chain transfer agents of Formula II for controlled radical polymerization processes.

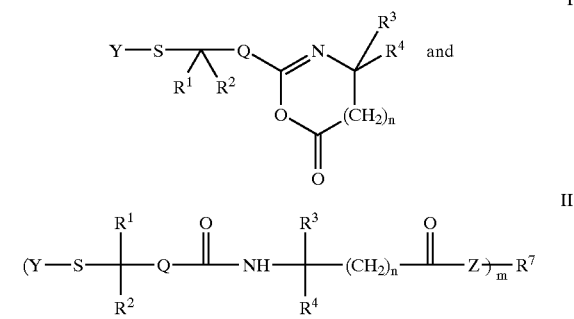

wherein $R^1$ and $R^2$ are each independently selected from H, an alkyl group of 1 to 18 carbon atoms, a nitrile, a cycloalkyl group having 3 to 14 carbon atoms, an aryl group having 6 to 14 ring atoms, an arenyl group having 6 to 26 carbon atoms, a heterocyclic group having one, two or three fused rings having 5 to 12 ring atoms and 1 to 3 heteroatoms selected from S, N, and nonperoxidic O; or $R^1$ and $R^2$ taken together with the carbon to which they are attached form a carbocyclic ring containing 4 to 12 ring atoms.

$R^3$ and $R^4$ are each independently selected from an alkyl group having 1 to 18 carbon atoms, a cycloalkyl group having 3 to 14 carbon atoms, an aryl group having 6 to 14 ring atoms, an arenyl group having 6 to 26 carbon atoms and 0 to 3 S, N, and nonperoxidic O heteroatoms, or $R^3$ and $R^4$ taken together with the carbon to which they are attached form a carbocyclic ring containing 4 to 12 ring atoms;

Y—S is a xanthate group of the formula $R^5$—O—C(S)—S—, a thioxanthate group of the formula $R^5$—S—C(S)—S, or a dithioester group of the formula $R^5$—C(S)—S—, wherein $R^5$ is selected from an alkyl group, a cycloalkyl group, an aryl group, an arenyl group or a heterocyclic group, $R^5$ is optionally substituted with phosphate, phosphonate, sulfonate, ester, halogen, nitrile, amide, and hydroxy groups; and $R^5$ may optionally be substituted with one or more caternary heteroatoms, such as oxygen, nitrogen or sulfur. Note Y—S may be abbreviated as "S—Y", or "SY".

Z is O, NH, S or $NR^8$, wherein $R^8$ is a H, an alkyl group, a cycloalkyl group, an aryl group an arenyl group or a heterocyclic group;

$R^7$ is an organic or inorganic moiety and has a valency of m;

m is an integer of at least 1, preferably 1 to 8, most preferably at least 2;

Q is a linking group selected from a covalent bond, an aryl group, an arenyl group, (—$CH_2$—)$_o$, —CO—O—($CH_2$)$_o$—, —CO—O—($CH_2CH_2O$)$_o$—, —CO—$NR^8$—($CH_2$)$_o$—, —CO—S—($CH_2$)$_o$—, where o is 1 to 12, and $R^8$ is H, an alkyl group, a cycloalkyl group, a heterocyclic group, or an aryl group;

and n is 0 or 1.

Chain transfer agents of Formula I may be prepared using the generalized sequence as shown:

Encyclopedia of Polymer Science and Engineering, vol. 11, $2^{nd}$ Ed., John Wiley and Sons, pp. 558–571 (1988). With respect to the above reaction scheme, it will be apparent that diacyl halide starting materials may be used to produce dimeric or bis-azlactone chain transfer agents. These bis-azlactone chain transfer agents have the general structure:

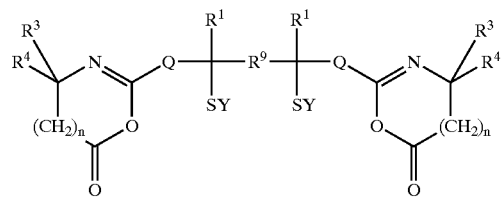

wherein

Y—S is a xanthate group of the formula $R^5$—O—C(S)—S—, a thioxanthate of the formula $R^5$—S—C(S)—S—, or a dithioester group of the formula $R^5$—C(S)—S—, wherein $R^5$ is selected from an alkyl group, a cycloalkyl group, an aryl group, an arenyl group or a heterocyclic group, $R^5$ is optionally substituted with phosphate, phosphonate, sulfonate, ester, halogen, nitrile, amide, and hydroxy groups; and $R^5$ may optionally be substituted with one or more caternary heteroatoms, such as oxygen, nitrogen or sulfur;

$R^1$ is selected from H, an alkyl group of 1 to 18 carbon atoms, a cycloalkyl group having 3 to 14 carbon atoms, an aryl group having 6 to 14 ring atoms, an arenyl group having 6 to 26 carbon atoms, a heterocyclic group having one, two or three fused rings having 5 to 12 ring atoms and 1 to 3 heteroatoms selected from S, N, and nonperoxidic O;

Scheme I

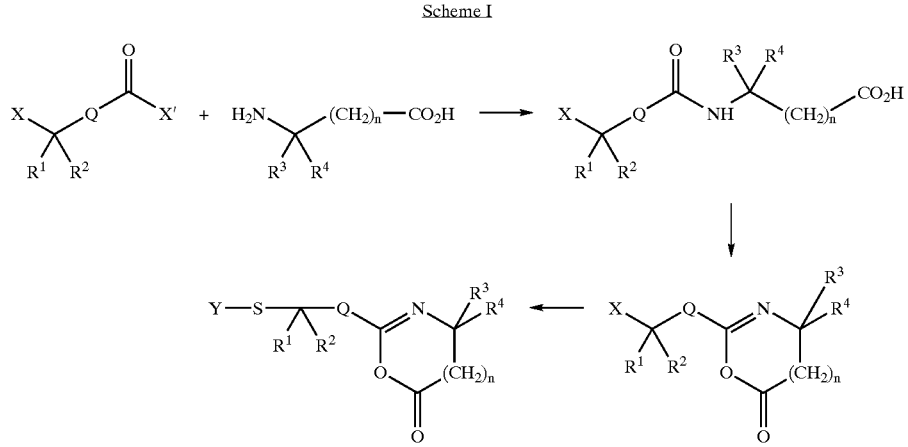

In the above Scheme 1, where X and X' are halogen atoms or other suitable leaving groups, an amino acid is first acylated, generally by dissolving the amino acid in aqueous base, followed by treatment with the acyl halide compound under interfacial reaction conditions. Cyclization may be effected by treatment with acetic anhydride and pyridine, by treatment with carbodiimides, or preferably by treatment with ethyl chloroformate and a trialkylamine, which proceeds through a mixed carboxyli-carbonic anhydride. The "Y—S" moiety is introduced by displacement of the X group, by a xanthic acid salt, a thioxanthic acid salt or a dithiocarboxylate salt. Further details regarding the preparation of azlactones may be found in "Polyazlactones", $R^3$ and $R^4$ are each independently selected from an alkyl group having 1 to 18 carbon atoms, a cycloalkyl group having 3 to 14 carbon atoms, an aryl group having 6 to 14 ring atoms, an arenyl group having 6 to 26 carbon atoms and 0 to 3 S, N, and nonperoxidic O heteroatoms, or $R^3$ and $R^4$ taken together with the carbon to which they are attached form a carbocyclic ring containing 4 to 12 ring atoms;

$R^9$ is a divalent alkylene group of 1 to 18 carbon atoms, a cycloalkylene group having 3 to 14 carbon atoms, an aryl group having 6 to 14 ring atoms, a heterocyclic group, or an arenyl group having 6 to 26 carbon atoms, Q is a linking group selected from a covalent bond, (—CH$_2$—)$_o$, —CO—O—(CH$_2$)$_o$—, —CO—O—(CH$_2$CH$_2$O)$_o$—, —CO—NR$^8$—(CH$_2$)$_o$—, —CO—S—(CH$_2$)$_o$—, where o is 1 to 12, and R$^8$ is H, an alkyl group, a cycloalkyl group, an arenyl group, a heterocyclic group or an aryl group; and n is 0 or 1.

Useful azlactone chain transfer agents include the following compounds:

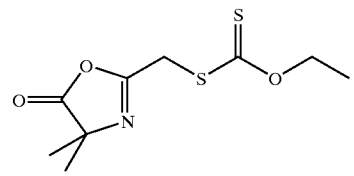

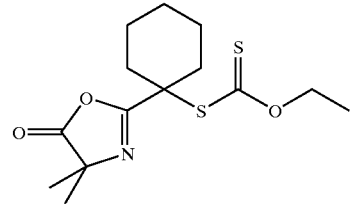

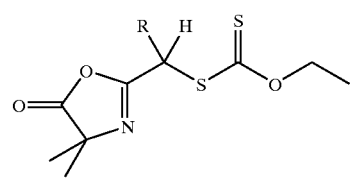

R = Me, CN, or Ph

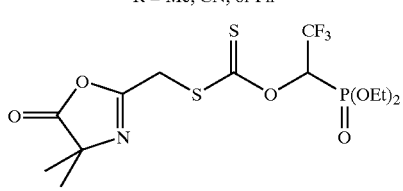

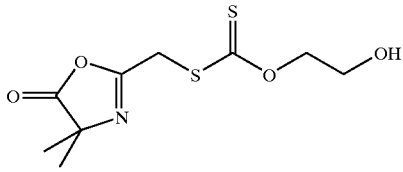

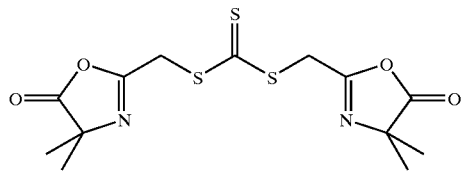

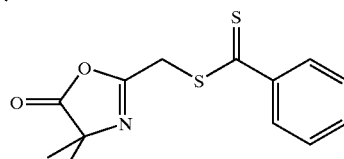

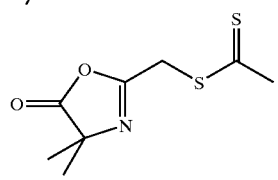

Ring-opened azlactone compounds of Formula II may be made by nucleophilic addition of a compound of the formula R$^7$(ZH)$_m$ to the azlactone carbonyl of Formula I as shown below. In the Scheme II, R$^7$ is an inorganic or organic group having one or a plurality of nucleophilic —ZH groups, which are capable of reacting with the azlactone moiety of Formula I. R$^7$(ZH)$_m$ may be water.

Scheme II

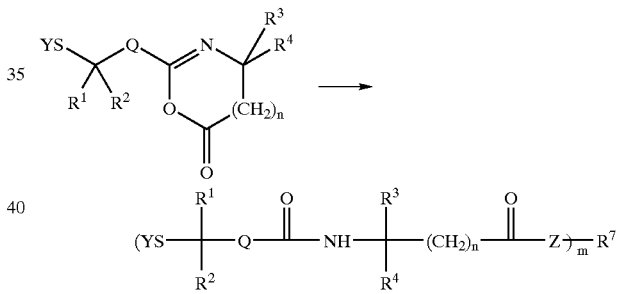

Alternatively, such ring opened compounds may be prepared by nucleophilic addition of a compound of the formula R$^7$(ZH), to the halogen-containing ("X") azlactone, followed by displacement of the X group with the "SY" group (by a xanthic acid salt, a thioxanthic acid salt or dithiocarboxylic acid salt), as shown in Scheme III.

Scheme III

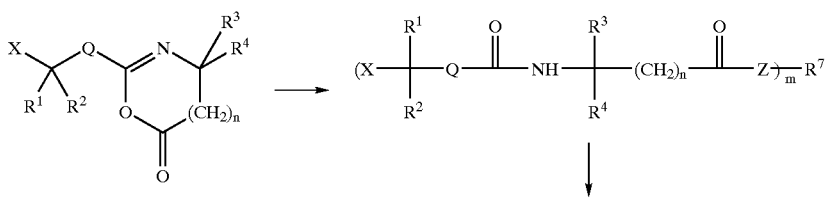

-continued

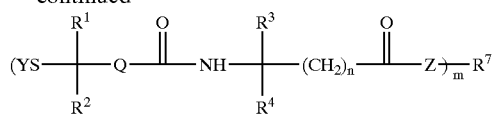

If organic, $R^7$ may be a polymeric or non-polymeric organic group that has a valence of m and is the residue of a nucleophilic group-substituted compound, $R^7(ZH)_m$, in which Z is —O—, —S—, or —NR wherein $R^8$ can be a H, an alkyl, a cycloalkyl or aryl, a heterocyclic group, an arenyl and m is at least one, preferably at least 2. The organic moiety R is preferably selected from mono- and polyvalent hydrocarbyl (i.e., aliphatic and aryl compounds having 1 to 30 carbon atoms and optionally zero to four heteroatoms of oxygen, nitrogen or sulfur), polyolefin, polyoxyalkylene, polyester, polyolefin, poly(meth)acrylate, or polysiloxane backbones. If inorganic, $R^7$ may comprise silica, alumina or glass having one or a plurality of —ZH groups on the surface.

In one embodiment, $R^7$ comprises a non-polymeric aliphatic, cycloaliphatic, aromatic or alkyl-substituted aromatic moiety having from 1 to 30 carbon atoms. In another embodiment, $R^7$ comprises a polyoxyalkylene, polyester, polyolefin, poly(meth)acrylate, polystyrene or polysiloxane polymer having pendent or terminal reactive —ZH groups. Useful polymers include, for example, hydroxyl, thiol or amino terminated polyethylenes or polypropylenes, hydroxyl, thiol or amino terminated poly(alkylene oxides) and poly(metb)acylates having pendant reactive functional groups, such as hydroxyethyl acrylate polymers and copolymers.

Depending on the nature of the functional group(s) of $R^7(ZH)_m$, a catalyst may be added to effect the condensation reaction. Normally, primary amine groups do not require catalysts to achieve an effective rate. Acid catalysts such as trifluoroacetic, ethanesulfonic, and toluenesulfonic acids are effective with hydroxyl groups and secondary amines. Basic catalysts such as DBU (1,8-diazabicyclo[5.4.0]undec-7-ene) and DBN are also effective.

With respect to the compound $R^7(ZH)_m$, m is at least one, but preferably m is at least two. The multiple —ZH groups of the polyfunctional compound may be the same or different. Multifunctional compounds may be reacted with the azlactone compound of Formula I to produce polyfunctional chain transfer agents of Formula II, where m is at least two. Such polyfunctional chain transfer agents allow the preparation of graft, branched, and star (co)polymers and other useful topologies.

Useful alcohols of the formula $R^7(ZH)_m$ include aliphatic and aromatic monoalcohols and polyols. Useful monoalcohols include methanol, ethanol, octanol, decanol, and phenol. The polyols useful in the present invention include aliphatic or aromatic polyols having at least two hydroxyl groups. Examples of useful polyols include ethylene glycol, propylene glycol, butanediol, 1,3-pentane diol, 2,2-oxydiethanol, hexanediol, poly(pentyleneadipate glycol), poly(tetramethylene ether glycol), poly(ethylene glycol), poly(caprolactone diol), poly(1,2-butylene oxide glycol), trimethylol ethane, trimethylol propane, trimethyol aminomethane, ethylene glycol, 2-butene-1,4-diol, pentaerythritol, dipentaerythritol, and tripentaerythritol. The term "polyol" also includes derivatives of the above-described polyols such as the reaction product of the polyol with di- or poly-isocyanate, or di- or poly-carboxylic acid, the molar ratio of polyol to —NCO, or —COOH being at least 1 to 1.

Useful amines of the formula $R^7(ZH)_m$ include aliphatic and aromatic monoamines and polyamines. Any primary or secondary amine may be employed, although primary amines are preferred to secondary amines. Useful monoamines include, for example, methyl-, ethyl-, propyl-, hexyl-, octyl, dodecyl-, dimethyl-, methyl ethyl-, and aniline. The term "di-, or polyamine," refers to organic compounds containing at least two non-tertiary amine groups. Aliphatic, aromatic, cycloaliphatic, and oligomeric di- and polyamines all are considered useful in the practice of the invention. Representative of the classes of useful di- or polyamines are 4,4'-methylene dianiline, 3,9-bis-(3-aminopropyl)-2,4,8,10-tetraoxaspiro[5,5]undecane, and polyoxyethylenediamine. Many di- and polyamines, such as those just named, are available commercially, for example, those available from Huntsman Chemical, Houston, Tex. The most preferred di- or polyamines include aliphatic diamines or aliphatic di- or polyamines and more specifically compounds with two primary amino groups, such as ethylene diamine, hexamethylene diamine, dodecanediamine, and the like.

Useful thiols of the formula $R^7(ZH)_m$ include aliphatic and aromatic monothiols and polythiols Useful alkyl thiols include methyl, ethyl and butyl thiol, as well as 2-mercaptoethanol, 3-mercapto-1,2-propanediol, 4-mercaptobutanol, mercaptoundecanol, 2-mercaptoethylamine, 2,3-dimercaptopropanol, 3-mercaptopropyltrimethoxysilane, 2-chloroethanethiol, 2-amino-3-mercaptopropionic acid, dodecyl mercaptan, thiophenol, 2-mercaptoethyl ether, and pentaerythritol tetrathioglycolate. Useful soluble, high molecular weight thiols include polyethylene glycol di(2-mercaptoacetate), LP-3™ resins supplied by Morton Thiokol Inc. (Trenton, N.J.), and Permapol P3™ resins supplied by Products Research & Chemical Corp. (Glendale, Calif.) and compounds such as the adduct of 2-mercaptoethylamine and caprolactam.

The invention provides multifunctional chain transfer agents of Formula II, whereby an azlactone chain transfer agent of Formula I is ring-opened by a multireactive or multifunctional compound of the formula $R^7(ZH)_m$, where m is at least 2. Such multifunctional chain transfer agents may be used to produce branched, star and graft (co) polymers and other topologies. It will also be apparent that such (co)polymers may also be prepared by first polymerizing a monomer using the chain transfer agent of Formula I, to produce polymers having an azlactone group at one terminal end, and then subsequently reacting the polymers with a polyfunctional compound of the formula $R^7(ZH)_m$, where m is at least 2.

In another embodiment, the multifunctional chain transfer agents may comprise a solid support having a plurality of chain transfer agent moieties on the surface thereof. Such chain transfer agent-functionalized supports have the general structure (corresponding to Formula II):

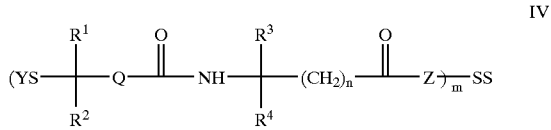

IV wherein Y—S, $R^1$, $R^2$, $R^3$, $R^4$, Q, Z, n and m are as previously described for Formula II and SS is a solid support corresponding to $R^7$. The solid support material includes functional groups to which chain transfer agent molecules of Formula I can be covalently attached for building large or small organic compounds. Useful functional groups include hydroxyl, amino and thiol functional groups corresponding to —ZH.

The support material can be organic or inorganic. It can be in the form of solids, gels, glasses, etc. It can be in the form of a plurality of particles (e.g., beads, pellets, or microspheres), fibers, a membrane (e.g., sheet or film), a disc, a ring, a tube, or a rod, for example. Preferably, it is in the form of a plurality of particles or a membrane. It can be swellable or non-swellable and porous or nonporous.

The support material can be a polymeric material that can be used in conventional solid phase synthesis. It is chosen such that it is generally insoluble in the solvents or other components used in synthetic reactions that occur during the course of solid phase synthesis. The support material can be a soluble or insoluble polymer having a molecular weight of 10,000 up to infinity for crosslinking polymers.

Examples of useable preexisting support materials are described in G. B. Fields et al., *Int. J. Peptide Protein Res.*, 35, 161 (1990) and G. B. Fields et al., in *Synthetic Peptides: A User's Guide*, G. A. Grant, Ed., pages 77–183, W.H. Freeman and Co., New York, N.Y. (1992). The support material is in the form of an organic polymeric material, such as polystyrenes, polyalkylenes, nylons, polysulfones, polyacrylates, polycarbonates, polyesters, polyimides, polyurethanes, etc. and having hydroxyl, amino or thiol substituents on the surface. For pre-existing support materials, a preferred support material is polystyrene.

In the present polymerization, the amounts and relative proportions of chain transfer agent and monomer are those effective to conduct radical polymerization. Accordingly, the amount of chain transfer agent can be selected such that the chain transfer agent concentration is from $10^{-5}$ M to 1M, preferably $10^{-4}$ to $10^{-2}$ M. Alternatively, the chain transfer agent can be present in a molar ratio of from $10^{-5}$:1 to $10^{-1}$:1, preferably from $10^{-5}$:1 to $2\times10^{-3}$:1, relative to monomer.

The initiator compositions of the present invention comprise the chain transfer agents of Formulas I or II and a thermal or photoinitiator.

Useful thermal initiators include azo, peroxide, persulfate, and redox initiators.

Suitable azo initiators include 2,2'-azobis(2,4-dimethylvaleronitrile) (VAZO™ 52); 2,2'-azobis (isobutyronitrile) (VAZO™ 64); 2,2'-azobis-2-methylbutyronitrile (VAZO™ 67); and (1,1'-azobis(I-cyclohexanecarbonitrile) (VAZO™ 88), all of which are available from DuPont Chemicals, and 2,2'-azobis(methyl isobutyrate) (V-601) and 2,2'-azobis(2-amidinopropane) dihydrochloride (V-50™) available from Wako Chemicals. Also suitable is 2,2'-azobis(4-methoxy-2,4-dimethylvaleronitrile), formerly available from DuPont Chemicals as VAZO™ 33.

Suitable peroxide initiators include benzoyl peroxide, acetyl peroxide, lauroyl peroxide, decanoyl peroxide, diacetyl peroxydicarbonate, di(4-t-butylcyclohexyl) peroxydicarbonate (PERKADOX™ 16S, available from AKZO Chemicals), di(2-ethylhexyl)peroxydicarbonate, t-butyl peroxybenzoate, t-butyl peroxypivalate (LUPERSOL™ 1, available from Atochem), t-butyl peroxy-2-ethylhexanoate (TRIGONOX™ 21-C50, available from Akzo Chemicals, Inc.), and dicumyl peroxide.

Suitable persulfate initiators include potassium persulfate, sodium persulfate, and ammonium persulfate.

Suitable redox (oxidation-reduction) initiators include combinations of the above persulfate initiators with reducing agents such as sodium metabisulfite and sodium bisulfite; systems based on organic peroxides and tertiary amines (for example, benzoyl peroxide plus dimethylaniline); and systems based on organic hydroperoxides and transition metals, for example, cumene hydroperoxide plus cobalt naphthenate.

Preferred thermal free-radical initiators are selected from the group consisting of azo compounds and peroxides, e.g., LUPERSOL™ 1 and PERKADOX 16, and mixtures thereof.

Useful photoinitiators are those capable of being activated by UV radiation, e.g., at wavelengths from about 250 nm to about 450 nm, more preferably at about 351 nm. Useful photoinitiators include e.g., benzoin ethers such as benzoin methyl ether and benzoin isopropyl ether, substituted benzoin ethers, arylphospine oxide, substituted acetophenones such as 2,2-dimethoxy-2-phenylacetophenone, and substituted alpha-ketols (alpha-hydroxyketones). Examples of commercially available photoinitiators include Irgacure™ 819 and Darocur™ 1173 (both available form Ciba-Geigy Corp., Hawthorne, N.Y.), Lucern TPO™ (available from BASF, Parsippany, N.J.) and Irgacure™ 651, (2,2-dimethoxy-1,2-diphenyl-1-ethanone), available from Ciba-Geigy corporation.

The thermal or photoinitiator is used in an amount effective to facilitate fragmentation of the azlactone chain transfer agent and the amount will vary depending upon, e.g., the type of initiator, and the monomer(s), and the desired molecular weight of the resulting (co)polymer. The initiators can be used in molar ratios from about 0.001:1 to 1:1, preferably 0.001:1 to 0.1:1 relative to the chain transfer agent. If desired, the initiator may be added in bulk, may be added intermittently, or may be continuously added. When preparing block copolymers, it is advantageous to add an initial charge of initiator with the chain transfer agent and monomer(s), polymerize to essential completion (i.e. depletion of the first monomer charge), then add additional initiator with the charge of a second monomer(s).

Examples of olefinically unsaturated monomers that may be polymerized include (meth)acrylic acid; (meth)acrylates such as ethyl (meth)acrylate, propyl (meth)acrylate, butyl (meth)acryl ate, isooctyl (meth)acrylate and other alkyl (meth)acrylates; also functionalized (meth)acrylates including glycidyl (meth)acrylate, poly(ethyleneoxide) (meth) acrylate, trimethoxysilyl propyl (meth)acrylate, allyl (meth) acrylate, hydroxyethyl (meth)acrylate, hydroxypropyl (meth)acrylate, mono- and dialkyl aminoalkyl (meth) acrylates; mercaptoalkyl (meth)acrylates, fluoroalkyl (meth) acrylates; (meth)acrylic acid, fumaric acid (and esters), itaconic acid (and esters), maleic anhydride; styrenics such as α-methyl styrene, functionailized styenes, t-butylstyrene, acetoxystyrene; vinyl halides such as vinyl chloride and vinyl fluoride; (meth)acrylonitrile, vinylidene halides; vinyl esters of carboxylic acids such as vinyl acetate and vinyl propionate; amides of vinyl amine such as vinyl formamide or vinyl acetamide; monomers containing a secondary, tertiary or quaternary amino group such as vinyl pyridine, butadienes; unsaturated alkylsulphonic acids or derivatives thereof; 2-vinyl-4,4-dimethylazlactone, N-vinyl pyrrolidinone. Mixtures of such monomers may be used.

Monomers having pendent, nucleophilic functional groups such as hydroxy-, amino- or thiol-functional groups are particularly useful for providing so-called $AB_n$ polymers. Such pendent nucleophilic functional groups may react with the azlactone terminal group to provide novel architectures. Such pendent nucleophilic functional groups may be protected during the polymerization, and deprotected post-polymerization for providing novel polymer architecture. In light initiated polymerizations, such functional groups may not required protection for subsequent thermal reaction.

Some of the above monomers, such as styrene, are autocatalytic; they will generate free radicals at elevated temperatures. Such monomers may be polymerized with the chain transfer agents without the addition of a thermal or photoinitiators.

The present polymerization may be conducted in bulk, or in a solvent. Solvents, preferably organic, can be used to assist in the dissolution of the chain transfer agent in the polymerizable monomers, and as a processing aid. Preferably, such solvents are not reactive with the azlactone group. Suitable solvents include ethers such as diethyl ether, ethyl propyl ether, dipropyl ether, methyl t-butyl ether, di-t-butyl ether, glyme (dimethoxyethane), diglyme, diethylene glycol dimethyl ether; cyclic ethers such as tetrahydrofuran and dioxane; alkanes; cycloalkanes; aromatic hydrocarbon solvents such as benzene, toluene, o-xylene, m-xylene, p-xylene; halogenated hydrocarbon solvents; acetonitrile; lactones such as butyrolactone, and valerolactones; ketones such as acetone, methyl ethyl ketone, methyl isobutyl ketone, cyclopentanone, and cyclohexanone; sulfones such as tetramethylene sulfone, 3-methylsulfolane, 2,4-dimethylsulfolane, butadiene sulfone, methyl sulfone, ethyl sulfone, propyl sulfone, butyl sulfone, methyl vinyl sulfone, 2-(methylsulfonyl)ethanol, and 2,2'-sulfonyldiethanol; sulfoxides such as dimethyl sulfoxide; cyclic carbonates such as propylene carbonate, ethylene carbonate and vinylene carbonate; carboxylic acid esters such as ethyl acetate, Methyl Cellosolve™ and methyl formate; and other solvents such as methylene chloride, nitromethane, acetonitrile, glycol sulfite and mixtures of such solvents, and supercritical solvents (such as $CO_2$). The present polymerization may be conducted in accordance with known polymerization processes.

Polymerizing may be conducted at a temperature of from −78 to 200° C. Autocatalytic monomers may be polymerized at temperatures above their respective autoinitiation temperatures. Styrene, for example, may be polymerized at temperatures above about 110° C. in the absence of initiator. Polymerization with thermal initiators may be preferably conducted from 0 to 160° C. and most preferably from 0 to 80° C. The reaction should be conducted for a length of time sufficient to convert at least 1% of the monomer to polymer. Typically, the reaction time will be from several minutes to 5 days, preferably from 30 minutes to 3 days, and most preferably from 1 to 24 hours.

Polymerizing may be conducted at a pressure of from 0.1 to 100 atmospheres, preferably from 1 to 50 atmospheres and most preferably at ambient pressure (although the pressure may not be measurable directly if conducted in a sealed vessel). An inert gas such as nitrogen or argon may be used.

While not wishing to be bound by theory, it is believed that the polymerization occurs by the following sequence:

Initiation

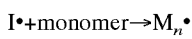
I•+monomer→$M_n$•

Chain transfer

$M_n$•+YS-Az⇌[YS-$M_n$-Az]•⇌YS-$M_n$+Az•

Reinitiation

Az•+monomer→Az-$M_m$•

Chain equilibration

Az-$M_m$•+YS-$M_n$⇌[Az-$M_m$-YS-$M_n$]⇌Az-$M_m$-SY+$M_n$•

In the above scheme, a propagating polymer radical $M_n$•, adds to the chain transfer agent, YS-Az, to generate a new radical, [YS-$M_n$-Az]•. This intermediate radical either fragements into a new propagating radical Az• and a new dormant species YS-$M_n$, or back to $M_n$• and YS-Az. The RAFT chain transfer agent establishes a dynamic addition-fragmentation equilibrium by transferring activity between the propagating radicals and the dormant species.

The (co)polymers obtained by the method of the invention may be described as telechelic (co)polymers comprising polymerized units of one or more free radically (co)polymerizable monomers (as previously described), a first azlactone terminal group derived from the chain transfer agent of Formula I and a second terminal group selected from a xanthate group, a thioxanthate group or a dithioester group (derived from "YS" group). Alternatively, when using the chain transfer agents of Formula II, the first terminal group "Az" will comprise the ring-opened residue of the azlactone group of the Formula III:

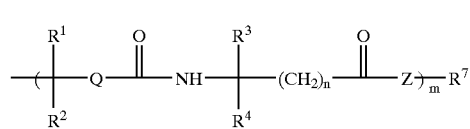

where $R^1$, $R^2$, $R^3$, $R^4$, $R^7$, Z, Q, m and n are as previously defined.

Such (co)polymers have the general formula Az-$(M^1)_x$ $(M^2)_x(M^3)_x$ . . . $(M^\Omega)_x$—S—Y, wherein "SY" is a xanthate group, a thioxanthate group or a dithioester group as defined in Formulas I and II; $M^1$ to $M^\Omega$ are each polymerized monomer units derived from a radically (co)polymerizable monomer unit having an average degree of polymerization x, each x is independent, and Az is an azlactone group or a ring-opened azlactone group of Formula III. Further, the polymer product retains the functional group "YS" at one terminal end of the polymer necessary to initiate a further polymerization (or functionalizalion). The polymer product further comprises either the azlactone moiety or the ring-opened azlactone moiety of the chain transfer agent at the other terminal end, which may be further reacted or functionalized as desired. Because the two terminal moieties have different functionality and reactivity, each terminus may be independently functionalized.

The terminal "Y—S" group may be functionalized independently from the terminal "Az" group. For example, functionalization of the azlactone followed by mild hydrolysis of the "YS" groups yields thiols, which readily oxidize to form a dimeric polymer linked by a disulfide group. Reduction of the disulfide linkage to yields a thiol group, which then may be further functionalized. Further, it has been discovered that hydroxy-, amino- and thio-compounds add preferentially to the azlactone terminal group rather than the "YS" terminal group, allowing independent functionalization. The first and second terminal groups of the (co)polymers may be used to functional the surface of a solid support, by judicicious choice of a co-reactive functional group on the surface of the support.

The present invention encompasses a novel process for preparing random, block, multi-block, star, gradient, random hyperbranched and dendritic copolymers, as well as graft or "comb" copolymers. Each of these different types of copolymers will be described hereunder.

Since RAFT polymerization is a "living" or "controlled" polymerization, it can be initiated and terminated as desired. Thus, in one embodiment, once the first monomer is consumed in the initial polymerizing step, a second monomer can then be added to form a second block on the growing polymer chain in a second polymerizing step. Additional polymerizations with the same or different monomer(s) can be performed to prepare multi-block copolymers.

Because RAFT polymerization is a radical polymerization, blocks can be prepared in essentially any order. One is not necessarily limited to preparing block copolymers where the sequential polymerizing steps must flow from the least stabilized polymer intermediate to the most stabilized polymer intermediate, such as is necessary in ionic polymerization. Thus, one can prepare a multi-block copolymer in which a polyacrylonitrile or a poly(meth) acrylate block is prepared first, then a styrene or butadiene block is attached thereto, etc.

Furthermore, a linking group is not necessary to join the different blocks of the present block copolymer. One can simply add successive monomers to form successive blocks. Further, it is also possible (and in some cases advantageous) to first isolate a (co)polymer produced by the present chain transfer agent polymerization process, then react the polymer with an additional monomer. In such a case, the product polymer having a terminal "Y—S" group acts as the new chain transfer agent for the further polymerization of the additional monomer.

Since the novel chain transfer agents provide a reactive group "Az" at a terminal end of the polymer, linking groups may be used to join two polymer blocks. For example, in one embodiment, a polymer prepared in accord with the present invention, and having an azlactone group at one terminus, may be reacted with a second polymer block having a nucleophilic terminal group.

Statistical copolymers may be produced using the chain transfer agents of the present invention. Such copolymers may use two or more monomers in a range of about 0–100% by weight of each of the monomers used. The product copolymer will be a function of the molar amounts of the monomers used and the relative reactivity of the monomers.

The present invention also provides graft or "comb" copolymers. Here, a first (co)polymer having pendent nucleophilic functional groups, such as hydroxy-, amino- or thio-groups, etc. is provided. An example of useful (co) polymers include hydroxyethyl acrylate (co)polymers. Next, the reactive functional groups of the first (co)polymer is reacted with the azlactone chain transfer agents of Formula I to provide a (co)polymer having pendent, ring-opened chain transfer agent moieties, the reaction product having the structure of Formula II, where $R^7$ is the residue of the first (co)polymer. This product (co)polymer may then be used as an chain transfer agent to polymerize the previously-described monomers to produce a comb (co)polymer. Alternatively, the first (co)polymer may be reacted with a telechelic (co)polymer of the invention, whereby the reactive "Az" terminal group reacts with the pendent reactive group of the first (co)polymer.

Gradient or tapered copolymers can be produced using RAFT polymerization by controlling the proportion of two or more monomers being added. For example, one can prepare a first block or an oligomer of a first monomer, then a mixture of the first monomer and a second distinct monomer can be added in proportions of from, for example, 1:1 to 9:1 of first monomer to second monomer. After conversion of all monomer(s) is complete, sequential additions of first monomer-second monomers mixtures can provide subsequent "blocks" in which the proportions of first monomer to second monomer vary. Thus, the invention provides copolymers obtained from two or more radically (co) polymerizable monomers wherein the copolymer has a composition that varies along the length of the polymer chain from azlactone terminus to opposite terminus based on the relative reactivity ratios of the monomers and instantaneous concentrations of the monomers during polymerization.

EXAMPLES

All reagents and solvents, unless otherwise noted, were purchased from Aldrich (Milwaukee, Wis.) and were used in their delivered condition. Polymerizable reagents were stripped of inhibitors prior to use by passing them through an alumina column (also supplied by Aldrich). Solvents were purchased from EM Science located in Gibbstown, N.J.

Compounds described in the Examples were found to have $^1$H NMR and IR spectra that were consistent with the assigned structure.

Preparative Example 1

Preparation of 2-(2-Chloro-acetylamino)-2-methyl propionic acid

To a stirring mixture of 2-aminoisobutyric acid (165.8 g; 1.61 mol), sodium hydroxide (64.4 g; 1.61 mol) and 800 mL water, cooled to 5° C., was added chloroacetyl chloride (200 g; 1.77 mol) and then a solution of sodium hydroxide (70.8 g; 1.77 mol) in 143 mL water. The temperature was maintained between 5 to 10° C. during the additions. The reaction mixture was then allowed to warm to room temperature and the solution was acidified with 165 mL of concentrated aqueous HCl. The precipitated solid was filtered and dried under vacuum to afford 180.4 g (62%) of product.

Preparative Example 2

Preparation of 2-Chloromethyl-4,4-dimethyl-4H-oxazol-5-one

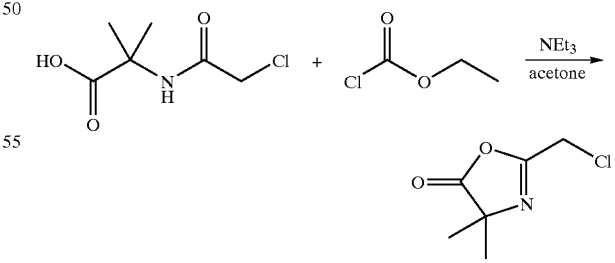

To a stirring mixture of 2-(2-chloro-acetylamino)-2-methyl propionic acid (18.0 g; 0.10 mol), triethylamine (11.1 g; 0.11 mol) and 100 mL acetone, cooled with an ice bath, was added ethyl chloroformate (10.5 mL; 0.11 mol) over a period of 10 minutes. The reaction mixture was then allowed to warm to room temperature and was stirred for 2 hours.

The mixture was then filtered, and the filtrate was concentrated under vacuum. Hexane (200 mL) was added to the residue, and the mixture was filtered. After removal of the solvent under vacuum, the filtrate residue was distilled under reduced pressure (59–60° C.; 7 mmHg) to give 13.2 g (82%) of a colorless oil.

Preparative Example 3

Preparation of 2-(2-Bromo-propionylamino)-2-methyl-propionic acid

To a stirring mixture of 2-aminoisobutyric acid (52.08 g; 0.51 mol), sodium hydroxide (20.20 g; 0.51 mol), 200 mL water and 50 mL chloroform cooled to −12° C., was added a solution of 2-bromopropionyl bromide (100 g; 0.463 mol) in 150 mL chloroform. The temperature was maintained between −15 to −12° C. during the addition. The reaction mixture was then allowed to warm to room temperature and stirred for 17 hours. The precipitated solid was filtered, mixed with 700 mL hot toluene, then cooled to room temperature. The solid was filtered and dried under vacuum to afford 77.6 g (70%) of product.

Preparative Example 4

Preparation of 2-(1-Bromo-ethyl)-4,4-dimethyl-4H-oxazol-5-one

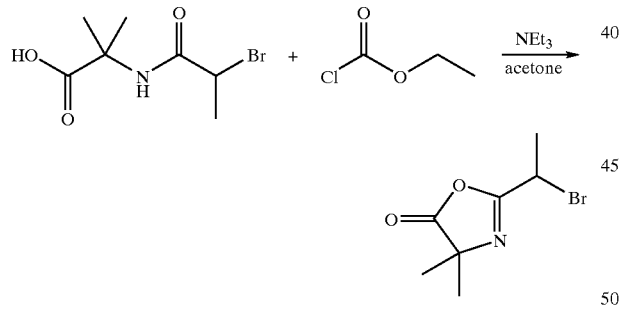

To a stirring mixture of 2-(2-bromo-propionylamino)-2-methyl-propionic acid (50.0 g; 0.21 mol), triethylamine (23.37 g; 0.23 mol) and 150 mL acetone, cooled with an ice bath, was added a solution of ethyl chloroformate (25.07 g; 0.23 mol) in 40 mL acetone over a period of 10 minutes. The reaction mixture was then allowed to warm to room temperature and was stirred for 2 hours. The mixture was then filtered, and the solid was washed with 150 mL ether. The combined filtrate was concentrated under vacuum. Ether (100 mL) was added to the residue, and the mixture was filtered. After removal of the solvent under vacuum, the filtrate residue was distilled under reduced pressure (63–64° C.; 1 mmHg) to give 34.73 g (75%) of a colorless oil.

Preparative Example 5

Preparation of N-[2-(Bis-{2-[2-(2-chloro-acetylamino)-2-methyl-propionylamino]-ethyl}-amino)-ethyl]-2-(2-chloro-acetylamino)-2-methyl-propionamide

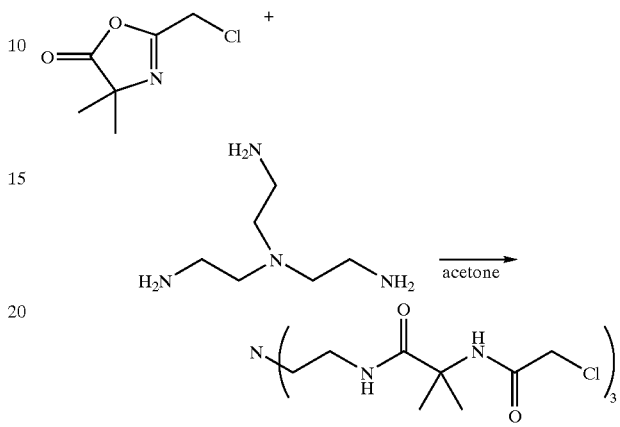

To a solution of 2-chloromethyl-4,4-dimethyl-4H-oxazol-5-one (2.00 g; 12.4 mmol) in 35 mL acetone was added dropwise a solution of tris(2-aminoethyl)amine in 2 mL acetone. The mixture was stirred for 30 minutes, then concentrated under vacuum to give 2.30 g (89%) of a yellow solid.

Example 1

Preparation of dithiocarbonic acid S-(4,4-dimethyl-5-oxo-4,5-dihydro-oxazol-2-ylmethyl)ester O-ethyl ester (AzTC)

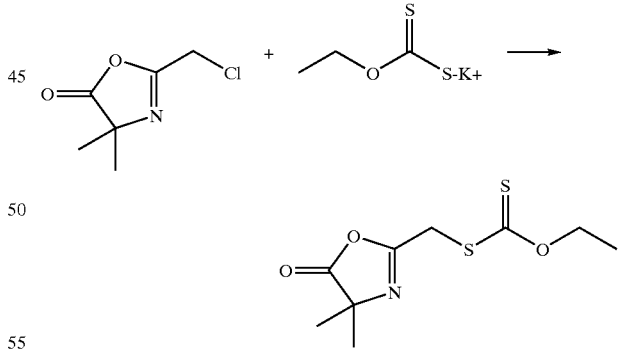

To a solution of 2-chloromethyl-4,4-dimethyl-4H-oxazol-5-one (15.67 g; 97 mmol) and 125 mL acetonitrile was added O-ethyl xanthic acid potassium salt (15.55 g; 97 mmol). The mixture was stirred under a nitrogen atmosphere at room temperature for 16 hours. The reaction mixture was filtered and the solid was washed with 50 mL acetonitrile. The combined filtrate was concentrated under reduced pressure to afford 21.79 g (91%) of AzTC as a yellow crystalline solid.

Example 2

Preparation of dithiocarbonic acid S-[1-(4,4-dimethyl-5-oxo-4,5-dihydro-oxazol-2-yl)-ethyl]ester O-ethyl ester

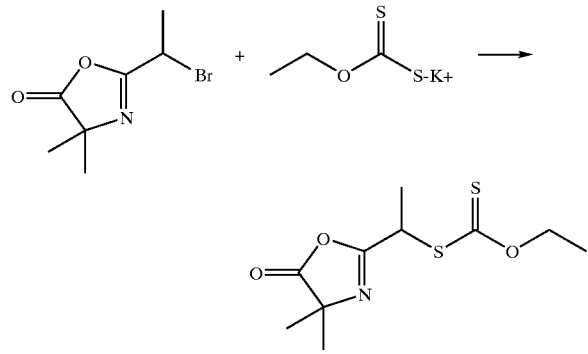

To a solution of 2-(1-bromo-ethyl)-4,4-dimethyl-4H-oxazol-5-one (3.00 g; 13.6 mmol) and 50 mL acetonitrile was added O-ethyl xanthic acid potassium salt (2.18 g; 13.6 mmol). The mixture was stirred under a nitrogen atmosphere at room temperature for 5 hours. The reaction mixture was filtered and the solid was washed with 10 mL acetontrile 10 mL. The combined filtrate was concentrated under reduced pressure to afford 2.89 g (81%) of dithiocarbonic acid S-[1-(4,4-dimethyl-5-oxo-4,5-dihydro-oxazol-2-yl)-ethyl] ester O-ethyl ester as a yellow oil.

Example 3

Preparation of Dithiocarbonic acid S-({1-[2-(bis-{2-[2-(2-ethoxythiocarbonylsulfanyl-acetylamino)-2-methyl-propionylamino]-ethyl}-amino) ethylcarbamoyl]-1-methyl-ethylcarbamoyl}-methyl) ester O-ethyl ester(tris(ring-opened AzTC)amine)

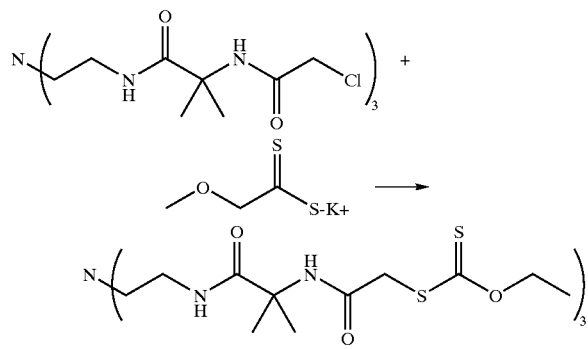

To a mixture of N-[2-(bis-{2-[2-(2-chloro-acetylamino)-2-methyl-propionylamino]-ethyl}-amino)-ethyl]-2-(2-chloro-acetylamino)-2-methyl-propionamide (1.00 g; 1.54 mmol) and 20 mL acetonitrile was added O-ethyl xanthic acid potassium salt (0.761 g; 4.75 mmol). After stirring the mixture at room temperature for 5 hr, additional O-ethyl xanthic acid potassium salt (0.370 g; 2.31 mmol) was added. After stirring for an additional 5 hours at room temperature, the mixture was filtered. The filtrate was concentrated under reduced pressure to to afford 1.20 g (87%) of the tris(ring-opened AzTC)amine as a red solid.

Example 4

Synthesis of Az-P(EHA)-TC via the Controlled Polymerization of 2-Ethylhexyl Acrylate with AzTC A solution of 0.305 g (1.23 mmol) of the product of Example 1 (AzTC), 8.59 g 2-ethylhexyl acrylate, 17 mg 2,2'-azobisisobutyronitrile and 9.01 g ethyl acetate was placed in a screw cap vial. The solution was sparged with nitrogen for 20 minutes, and the vial was sealed. The vial was heated in an oil bath at 70° C. for 4.75 hours. A small aliquot of the reaction mixture was weighed and was then concentrated to dryness by heating in an oven at 50° C. for 16 hours. The ratio of the mass of each dried sample to the mass of the aliquot of reaction mixture was used to calculate the percent conversion of the monomer. The conversion was 97%. Analysis of the polymer by gel permeation chromatography in tetrahydrofuran showed $M_n$=5720 and polydispersity=1.88.

Example 5

Synthesis of Az-PSt-TC via the Controlled Polymerization of Styrene with Thiocarbonic acid S-[1-(4,4-dimethyl-5-oxo-4,5-dihydro-oxazol-2-yl)-ethyl]ester O-ethyl ester A solution 0.327 g (1.25 mmol) of the product of Example 2 (dithiocarbonic acid S-[1-(4,4-dimethyl-5-oxo-4,5-dihydro-oxazol-2-yl)-ethyl]ester O-ethyl ester), 5.00 g styrene and 0.40 g of a 2 wt % solution of 2,2'-azobisisobutyronitrile in ethyl acetate was placed in a screw cap vial. The solution was sparged with nitrogen for 25 minutes, and the vial was sealed. The vial was placed in an oven at 70° C. for 24 hours. The polymer was then precipitated into 50 mL petroleum ether. The liquid was decanted, and an additional 60 mL petroleum ether was added. The mixture was shaken for 24 hours, then the solvent was decanted. The recovered polymer was dried under vacuum (2.50 g). Analysis of the polymer by gel permeation chromatography in tetrahydrofuran showed $M_n$=2820 and polydispersity=1.84.

Example 6

Synthesis of Synthesis of Az-P(IBA)-TC via the Controlled Polymerization of 2-Ethylhexyl Acrylate with dithiocarbonic acid S-[1-(4,4-dimethyl-5-oxo-4,5-dihydro-oxazol-2-yl)-ethyl]ester O-ethyl ester A solution of 0.183 g (0.70 mmol) of the product of Example 2 (dithiocarbonic acid S-[1-(4,4-dimethyl-5-oxo-4,5-dihydro-oxazol-2-yl)-ethyl]ester O-ethyl ester), 5.00 g isobornyl acrylate, 5.70 g ethyl acetate and 0.46 g of a 2 wt % solution of 2,2'-azobisisobutyronitrile in ethyl acetate was placed in a screw cap vial. The solution was sparged with nitrogen for 20 minutes, then the vial was sealed. The vial was placed in an oven at 70° C. for 7 hours. The polymer was then precipitated into methanol and filtered. The recovered polymer was dried under vacuum. Analysis of the polymer by gel permeation chromatography in tetrahydrofuran showed $M_n$=3630 and polydispersity=1.83.

Example 7

Synthesis of a Poly(Isobornyl Acrylate) Star Polymer with Tris(ring-opened AzTC)amine A mixture of 0.105 g (0.12 mmol) of the product from Example 3 (tris(ring-opened AzTC)amine), 1.20 g isobornyl acrylate, 1.50 g tetrahydrofuran, and 0.369 g of a 2 wt % solution of 2,2'-azobisisobutyronitrile in ethyl acetate was placed in a screw cap vial. The solution was sparged with nitrogen for 5 minutes, then the vial was sealed. The vial was placed in an oven at 65° C. for 7 hours. The solution was then precipitated into 60 mL of methanol. The resultant white solid was filtered and dried under vacuum. Analysis of the polymer by gel permeation chromatography in tetrahydrofuran showed $M_n$=2930 and polydispersity=4.86. The polydispersity of the polymer is higher than expected due to a multimodal distribution of molecular weights. It is believed the multimodal distribution it is due to varying transfer from each arm, or premature termination of the chains from each arm, yielding multiple arm lengths.

Example 8

Synthesis of a Poly(2-Ethylhexyl Acrylate) Star Polymer with Az-P(EHA)-TC and Trimethylolpropane A solution of 0.154 g (0.62 mmol) of the product of Example 1 (AzTC), 4.30 g 2-ethylhexyl acrylate and 0.43 g of a 2 wt % solution of 2,2'-azobisisobutyronitrile in ethyl acetate was placed in a screw cap vial. The solution was sparged with nitrogen for 15 minutes, and the vial was sealed. The vial was heated in an oven at 70° C. for 3 hours. A small aliquot of the reaction mixture was weighed and was then concentrated to dryness by heating in an oven at 100° C. for 3 hours. The ratio of the mass of the dried sample to the mass of the aliquot of reaction mixture was used to calculate the percent conversion of the monomer. The conversion was 94%. Analysis of the polymer by gel permeation chromatography in tetrahydrofuran showed $M_n$=4825 and polydispersity=2.15.

An aliquot of the above polymer solution (1.00 g) was mixed with a solution of 0.0032 g (0.024 mmol) trimethylolpropane in 0.3 g ethyl acetate and 1 mg (0.007 mmol) 1,8-diazabicyclo[5.4.0]undec-7-ene. The solution was left to stand at room temperature for 48 hours. Analysis of the polymer solution by gel permeation chromatography in tetrahydrofuran showed $M_n$=6759 and polydispersity=2.25.

Example 9

Synthesis of Az-Poly(IBA-block-EHA)-TC via the Controlled Polymerization of 2-Ethythexyl Acrylate with Az-P(IBA)-TC A solution of 1.00 g (0.2 mmol) of the product of Example 6 (Az-P(IBA)-TC; $M_n$=3630; polydispersity=1.83), 2.00 g 2-ethylhexyl acrylate, 4.0 g ethyl acetate, and 0.15 g of a 2 wt % solution of 2,2'-azobisisobutyronitrile in ethyl acetate was placed in a screw cap vial. The solution was purged with nitrogen for 15 minutes, then the vial was sealed. The vial was placed in an oven at 70° C. for 4 hours. The solution was then precipitated into 150 mL of methanol. The liquid was decanted from the polymer and an additional 150 mL of methanol was added. The mixture was shaken for 24 hours, then the solvent was decanted. The recovered polymer was dried under vacuum. Analysis of the polymer by gel permeation chromatography in tetrahydrofuran showed $M_n$=9900 and polydispersity=2.88.

Example 10

Synthesis of Az-P(EHA)-TC via the Controlled Polymerization of 2-Ethylhexyl Acrylate with AzTC using UV Irradiation Solutions of 2-ethylhexyl acrylate, Darocur 1173™ (Ciba Specialty Chemical Corp., Tarrytown, N.Y.), and AzTC were mixed according to Table 10.1 and placed in screw cap vials. The solutions were sparged with nitrogen for 15 minutes, sealed, and rolled under an UV lamp (Sylvania F40/350BL) for 16 hours. Monomer conversion was 98% by gravimetric analysis. Analysis of the polymers by gel permeation chromatography in tetrahydrofuran is shown below.

TABLE 10.1

Solution Composition and Molecular Weight Determination for Example 10.

| Sample | EHA, g | Darocur 1173, g | AzTC, g | Mn, g/mol | polydispersity |
|---|---|---|---|---|---|
| 10-1 | 10.0 | 0.02 | 0.06 | 37,000 | 2.04 |
| 10-2 | 10.0 | 0.02 | 0.10 | 22,500 | 2.07 |

We claim:

1. A controlled radical polymerization chain transfer agent comprising a compound of the formula:

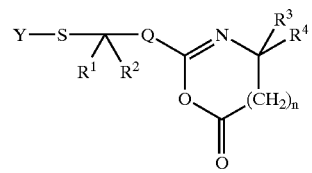

I wherein $R^1$ and $R^2$ are each independently selected from H, an alkyl group, a nitrile, a cycloalkyl group, a heterocyclic group, an arenyl group and an aryl group, or $R^1$ and $R^2$ taken together with the carbon to which they are attached form a carbocyclic ring;

$R^3$ and $R^4$ are each independently selected from an alkyl group, a cycloalkyl group, an aryl group, an arenyl group, a heterocyclic group or $R^3$ and $R^4$ taken together with the carbon to which they are attached form a carbocyclic ring;

Y—S is a xanthate group, a thioxanthate group, or a dithioester group;

Q is a linking group selected from a covalent bond, aryl group, (—CH$_2$—)$_o$, —CO—O—(CH$_2$)$_o$—, —CO—O—(CH$_2$CH$_2$O)$_o$—, —CO—NR$^8$—(CH$_2$)$_o$—, —CO—S—(CH$_2$)$_o$—, where o is 1 to 12, and $R^8$ is H, an alkyl group, a cycloalkyl group, and arenyl group, a heterocyclic group or an aryl group; and n is 0 or 1.

2. The chain transfer agent of claim 1, wherein Y—S is a xanthate group of the formula $R^5$—O—C(S)S—, a thioxanthate group of the formula $R^5$—S—C(S)S—, or a dithioester group of the formula $R^5$—C—(S)S—, wherein $R^5$ is selected from an alkyl group, a cycloalkyl group, an aryl group, or an arenyl group.

3. The chain transfer agent of claim 2 wherein at least one of $R_1$ and $R_2$ are methyl.

4. The chain transfer agent of claim 1 wherein at least one of $R_3$ and $R_4$ is a $C_1$ to $C_4$ alkyl group.

5. The chain transfer agent of claim 4 wherein $R_3$ and $R_4$ are methyl.

6. An initiator composition comprising the chain transfer agent of claim 1 and a thermal- or photoinitiator.

7. The initiator composition of claim 6 wherein said thermal initiator is selected from azo, peroxide, persulfate, and redox initiators.

8. The initiator composition of claim 6 wherein said photoinitiator is selected from benzoin ethers, substituted benzoin ethers, substituted acetophenones, arylphospine oxides, and substituted alpha-ketols.

9. The initiator composition of claim 6 wherein the molar ratio of initiator to chain transfer agent is from 0.001:1 to 0.1:1.

10. A method for addition polymerization of one or more olefinically unsaturated monomers comprising exposing a mixture of one or more olefinically unsaturated monomers and the chain transfer agent of claim 1 to radiant energy.

11. The method of claim 10 wherein said mixture further comprises a thermal or photoinitiator.

12. The method according to claim 10, wherein the olefinically unsaturated monomers are selected from (meth) acrylic acid; (meth)acrylates; fumaric acid (and esters), itaconic acid (and esters), maleic anhydride; styrene; styrenics; vinyl halides; (meth)acrylonitrile; vinylidene halides; vinyl esters of carboxylic acids; amides of vinyl amines; monomers containing a secondary, tertiary or quaternary amino group; butadienes; unsaturated alkylsulphonic acids or derivatives thereof; 2-vinyl-4,4-dimethylazlactone, and N-vinyl pyrrolidinone.

13. The method according to claim 10, wherein the polymerization is conducted neat or in a solvent.

14. The method according to claim 10 further comprising a second polymerizing step using one or more additional olefinically unsaturated monomers.

15. The method of claim 10, wherein the chain transfer agent is present in a concentration of from $10^{-5}$ M to 1 M.

16. The method of claim 10, wherein the molar ratio of chain transfer agent and monomer(s) is from $10^{-5}$:1 to $10^{-1}$:1 of chain transfer agent to monomer(s).

* * * * *

UNITED STATES PATENT AND TRADEMARK OFFICE
CERTIFICATE OF CORRECTION

PATENT NO. : 6,762,257 B1
APPLICATION NO. : 10/429487
DATED : July 13, 2004
INVENTOR(S) : Kevin M. Lewandowski It is certified that error appears in the above-identified patent and that said Letters Patent is hereby corrected as shown below:

Col. 1
Line 38, delete "RAF" and insert -- RAFT --, therefor.

Col. 2
Line 14, delete "hetcrocyclic" and insert
 -- heterocyclic --, therefor.
Line 23, delete "$R^5$—S—C(S)S—" and insert
 -- $R^5$—S—C(S)—S— --, therefor.
Line 24, delete "$R^5$—C(S)S—" and insert
 -- $R^5$—C(S)—S— --, therefor.
Lines 62-63, delete "$R^5$—S—C(S)S—" and insert
 -- $R^5$—S—C(S)—S— --, therefor.

Col. 3
Line 7, after "group" delete ",".
Line 13, delete "CO-O-($CH_2CH_2)_o$" and insert
 -- CO-O-($CH_2CH_2O)_o$ --, therefor.

Col. 5
Lines 8-9, delete "$R^5$—S—C(S)—S" and insert
 -- $R^5$—S—C(S)—S— --, therefor.
Line 63, delete "carboxyli" and insert
 -- carboxylic --, therefor.

Col. 8
Line 47, delete "$R^7$(ZH)," and insert -- $R^7(ZH)_m$ --, therefor.

Col. 9
Line 12, delete "NR" and insert -- $NR^8$ -- before "wherein".
Line 14, delete "R" and insert -- $R^7$ --, therefor.
Line 31, delete "poly(metb)acylates" and insert
 -- poly(meth)acylates --, therefor.

Col. 11
Line 30, delete "preexisting" and insert
 -- pre-existing --, therefor.

UNITED STATES PATENT AND TRADEMARK OFFICE
CERTIFICATE OF CORRECTION

PATENT NO. : 6,762,257 B1
APPLICATION NO. : 10/429487
DATED : July 13, 2004
INVENTOR(S) : Kevin M. Lewandowski It is certified that error appears in the above-identified patent and that said Letters Patent is hereby corrected as shown below:

Col. 14
Line 49, delete "functionalizalion" and insert
-- functionaization --, therefor.

Col. 19
Line 38, after "amino)" insert -- — --, therefor.

Col. 20
Line 52, delete "isobomyl" and insert -- isobornyl --, therefor.

Col. 21
Line 45, delete "Ethythexyl" and insert -- Ethylhexyl --, therefor.

Col. 22
Line 50, in Claim 2, delete "$R^5$—O—C(S)S—" and insert
-- $R^5$—O—C(S)—S— --, therefor.
Line 51, in Claim 2, delete "$R^5$—S—C(S)S—" and insert
-- $R^5$—S—C(S)—S— --, therefor.
Line 52, in Claim 2, delete "$R^5$—C—(S)S—" and insert
-- $R^5$—C(S)—S— --, therefor.

Col. 23
Line 1, in Claim 8, delete "arylphospine" and insert -- arylphosphine --, therefor.

Signed and Sealed this

Thirteenth Day of November, 2007

JON W. DUDAS
*Director of the United States Patent and Trademark Office*